(12) United States Patent
Zhang et al.

(10) Patent No.: US 8,846,627 B2
(45) Date of Patent: Sep. 30, 2014

(54) METHOD FOR TREATMENT OF MALARIA

(75) Inventors: Weidong Zhang, Shanghai (CN); Jin Huang, Shanghai (CN); Lei Shan, Shanghai (CN); Honglin Li, Shanghai (CN); Liyan Wang, Shanghai (CN); Shoude Zhang, Shanghai (CN); Weiqiang Lu, Shanghai (CN); Juan Su, Shanghai (CN); Tong Chen, Shanghai (CN)

(73) Assignees: The Second Military Medical University, Shanghai (CN); East China University of Science and Technology, Shanghai (CN)

( * ) Notice: Subject to any disclaimer, the term of this patent is extended or adjusted under 35 U.S.C. 154(b) by 4 days.

(21) Appl. No.: 13/452,962

(22) Filed: Apr. 23, 2012

(65) Prior Publication Data

US 2012/0295859 A1    Nov. 22, 2012

Related U.S. Application Data

(63) Continuation-in-part of application No. PCT/CN2010/001403, filed on Sep. 13, 2010.

(30) Foreign Application Priority Data

Oct. 21, 2009    (CN) .......................... 2009 1 0197473

(51) Int. Cl.
   *A61K 31/70*    (2006.01)
   *A61K 31/7048*    (2006.01)

(52) U.S. Cl.
   CPC .................................. *A61K 31/7048* (2013.01)
   USPC ........................................................ 514/27

(58) Field of Classification Search
   CPC ............................ A61K 31/7048; C07H 17/07
   USPC ................................................ 536/8; 514/27
   See application file for complete search history.

(56) References Cited

FOREIGN PATENT DOCUMENTS

CN    1733788 A    2/2006

OTHER PUBLICATIONS

Nowak, Renata, "Separation and Quantification of Tiliroside from Plant Extracts by SPE/RP-HPLC", Pharmaceutical Biology, 2003, vol. 41, No. 8, pp. 627-630.*
Lehane et al, "Common dietary flavonoids inhibit the growth of the intraerythrocytic malaria parasite", BioMed Central Research Notes, published online Jun. 18, 2008; 1:26.*
Hongmei Liu et al., Acylated Flavonol Glycosides From Leaves of *Stenochlaena palustris*, J. Nat. Prod., vol. 62, pp. 70-75 (1999).
Kaori Yoshida et al., Flavonol Caffeoylglycosides as α-Glucosidase Inhibitors From *Spiraea cantoniensis* flower, J. Agric. Food. Chem., vol. 56, pp. 4367-4371 (2008).
S.J. Bloor, An Antimicrobial Kaempferol-diacyl-rhamnoside From *Pentachondra pumila.*, Phytochemistry, vol. 38(4), pp. 1033-1035 (1995).
M. Jain et al., Synthesis, Anti-Malarial, Antileishmanil, and Antimicrobial Activities of Some 8-Quinolinamine Analogues, Bioorg. Med. Chem., vol. 13, pp. 4458-4466 (2005).
M.T. Makler et al., Measurement of the Lactate Dehydrogenase Activity of *Plasmodium falciparum* as an Assessment of Parasitemia, Am. J. Trop. Med. Hyg., vol. 48(2), pp. 205-210 (1993).
J. Mustafa et al., Synthesis and Anticancer Activities of Fatty Acid Analogs of Podophyllotoxin, Lipid, vol. 39(2), pp. 167-172 (2004).
D.A. Fidock et al., Antimalarial Drug Discovery: Efficacy Models for Compound Screening, Nature Reviews, vol. 3, pp. 509-520 (2004).

* cited by examiner

*Primary Examiner* — Elli Peselev
(74) *Attorney, Agent, or Firm* — Manni Li; Mei & Mark LLP

(57) ABSTRACT

A method for treatment of malaria including administering to a patient in need thereof a flavonoid glycoside compound.

3 Claims, 2 Drawing Sheets

METHOD FOR TREATMENT OF MALARIA

CROSS-REFERENCE TO RELATED APPLICATIONS

This application is a continuation-in-part of International Patent Application No. PCT/CN2010/001403 with an international filing date of Sep. 13, 2010, designating the United States, now pending, and further claims priority benefits to Chinese Patent Application No. 200910197473.4 filed Oct. 21, 2009. The contents of all of the aforementioned applications, including any intervening amendments thereto, are incorporated herein by reference.

BACKGROUND OF THE INVENTION

1. Field of the Invention

The invention relates to a method for treatment of malaria using a flavonoid glycoside compound.

2. Description of the Related Art

As the most frequent parasitosis on the earth, malaria is a potential deadly disease transmitted through anopheles. According to the World Health Organization (WHO), there are approximately 500 million cases of malaria, causing nearly one million deaths, mostly in Africa. It is estimated that a child under five years old dies every 30 seconds from the disease. Malaria is usually caused by *plasmodium*. After the bite of infected female anopheles, *plasmodium* is injected into human body. 10 to 20 days later, typical clinical manifestation shows, which can be classified to 4 phases: stadium frigoris stage, hyperpyrexia Stage, sweating stage and diapauses stage. After repeated paroxysm of malaria, anaemia, hepatomegaly, splenomegaly, even dangerous symptoms such as cerebral, ultrahyperpyrexia, cold syncope and gastrointestinal malaria may occur, which is serious even fatal to life. Due to the climbing of tolerance to the existing drugs, the incidence rate of malaria daily increases, which demand the invention of new type therapeutic anti-malaria drugs.

Plasmodia in erythrocytic stage would hydrolyze host hemoglobin in the acidic food vacuole to obtain necessary energy and amino acids. Biological studies indicate that plasmodia food vacuole possess a series of hydrolytic enzymes, such as plasmepsins, falcipains and falcilysins. These enzymes have become potential targets for malaria chemotherapy.

The molecular weight of falcipain is about 21,000 to 30,000. The highest hydrolytic activity presents at pH 4-6.5 and its active sites contain cysteine residues. *Plasmodium*'s falcipains belongs to the papain-family cysteine proteases. The known *plasmodium*'s falcipain proteins have four subtypes, which are falcipain-1, falcipain-2A, falcipain-2B and falcipan-3. In addition, falcipain 1 is the first *plasmodium* cysteine protease obtained by exogenous expression. Biological studies have shown that falcipain 1 has no effect on asexual stage of *plasmodium*, but has significant effects on ovarian function. Falcipain-2A and flacipain-2B have 97% homology and only differ in the seventh amino acid. Through the detection of oligonucleotide probes, the expression level of falcipain-2B mRNA is lower than falcipain-2A. However, in the late vegetative stage of *plasmodium*, the time-dependence and peak value of expression of falcipain-2A and falcipain-2B are very similar, which indicate that two different subtypes have similar biological function. Falcipain-3 and falcipain-2 have 66.6% homology in the catalytic domain, but express in different stage. The expression of falcipain-2 reaches a peak in the vegetative stage, but falcipain-3's expression peaks at more mature stage. In these subtypes, studies on falcipain-2 are broader and deeper, and therefore, and their inhibitors development are also subjected to more extensive attention.

It has been a long history since the Traditional Chinese Medicine was used to treat malaria. For example, according to the book *Suwen* about Acupuncture for Malaria, acupuncture was used to prevent malaria. A lot of Chinese herbs, not only *Artemisia apiacea*, are used as folk medicines against malaria, including *Clematis chinensis, Kyllinga brevifolia, Java Brucea, Antipyretic dichroa, Centipeda minima, Areca nut, Potentilla discolor, Ranunculus sceleratus*, et al. The compound artemisinine that is found in *Artemisia apiacea* show good effect in treating malaria. The investigators of this invention built a compound library with more than 2,000 natural compounds by years' hard work. By screening the compounds in the library, the investigators discovered a kind of flavonoid glycoside compounds with anti-malaria effect.

SUMMARY OF THE INVENTION

In view of the above-described problems, it is one objective of the invention to provide a method for treatment of malaria.

To achieve the above objective, in accordance with one embodiment of the invention, there is provided a method for treatment of malaria comprising administering to a patient in need thereof a flavonoid glycoside compound.

The structures of the flavonoid glycoside compound are represented by one of the general formulas (A) and (B).

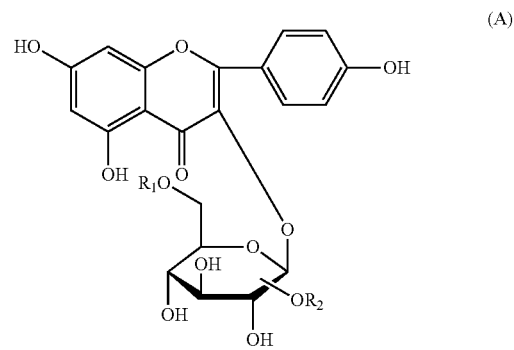

(A)

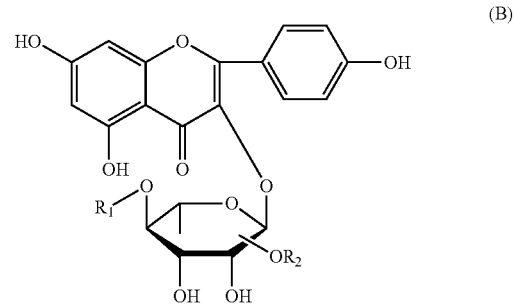

(B)

In the formulas (A) and (B), $R_1$ is coumaroyl, transcoumaroyl, or caffeoryl; $R_2$ is coumaroyl, transcoumaroyl, caffeoryl, or H.

The flavonoid glycoside compound is prepared by extraction from herbal medicines or by chemical synthesis.

The representative flavonoid glycoside compound disclosed in this invention comprises stenopalustroside A, stenopalustroside D, tiliroside, kaempferol 3-O-β-(6"-caffeoylglucoside), and kaempferol 3-(2,4-di-E-p-coumaroyl-rhamnoside).

Demonstrated by the experiments, these five flavonoid glycoside compounds have significant binding effect with FP-2 protein and in vitro anti-malarial activity against cultured *Plasmodium falciparum*, thus, can be used to manufacture pharmaceutical composition for treating malaria.

In another aspect, the invention provides a pharmaceutical composition comprising therapeutical dose of the flavonoid glycoside compound as an active ingredient and a pharmaceutically acceptable carrier. The content of the active ingredient is between 5.0% and 95.0% by weight.

The pharmaceutically acceptable carrier is related to the conventional drug carrier, such as diluents (water, starch, sugar, etc.), adhesives (cellulose derivatives, alginate, gelatin, polyvidone, etc.), wetting agents (glycerol, etc.), disintegrants (agar, $CaCO_3$, $NaHCO_3$, etc.), penetration enhancers (quaternary ammonium compound, etc.), surfactants (palmityl alcohol, etc.), adsorbents (kaolin, bentonite, etc.), lubricants (talc, calcium stearate, magnesium stearate, macrogol, etc.). Other excipients, such as scenting agents and sweeting agents can also be added in the pharmaceutically composition.

The compound and pharmaceutically composition disclosed in the invention can be administered to a patient in need thereof by mouth, by the intranasal route, per rectum, or parenterally. When administered orally, the compound or pharmaceutically composition can be prepared in tablets, powder, granule, gelatin capsule, or liquid preparation (water suspension, oil suspension, syrup, elixir, etc.). When administered parenterally, the compound or pharmaceutically composition can be prepared in solution, water suspension or oil suspension for injection. The priority form is tablets, coated tablets, gelatin capsule, suppository, nasal spray, or injection.

The dosage forms of the compound and pharmaceutically composition disclosed in the invention can be prepared by the conventional methods in pharmaceutical industry.

Figure 1:
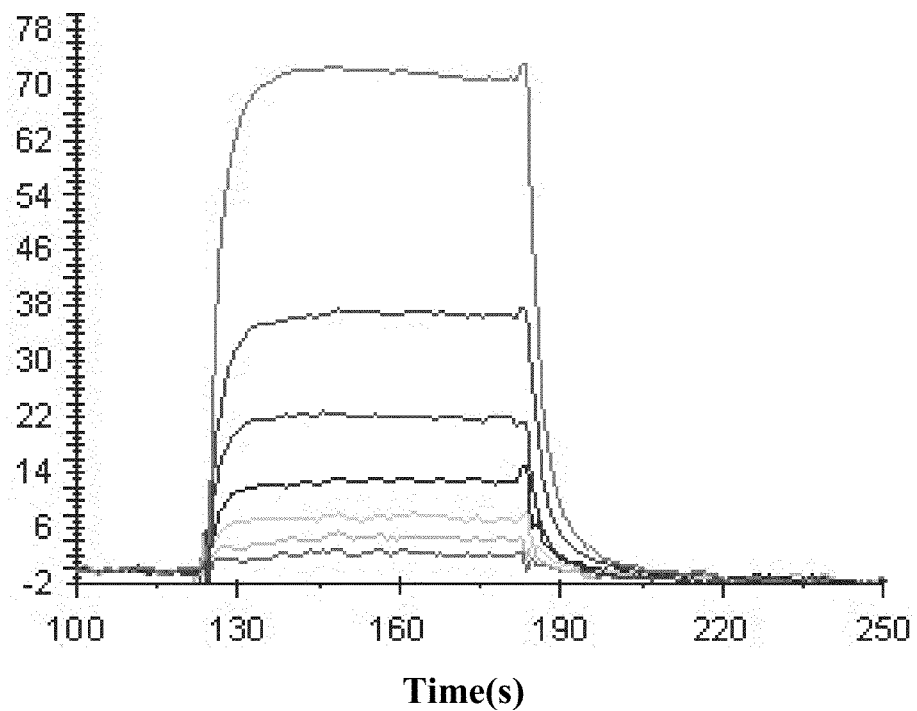
FIG. 1 is a response curve of an interaction between a positive control and FP-2 protein by SPR.
Figure 2:
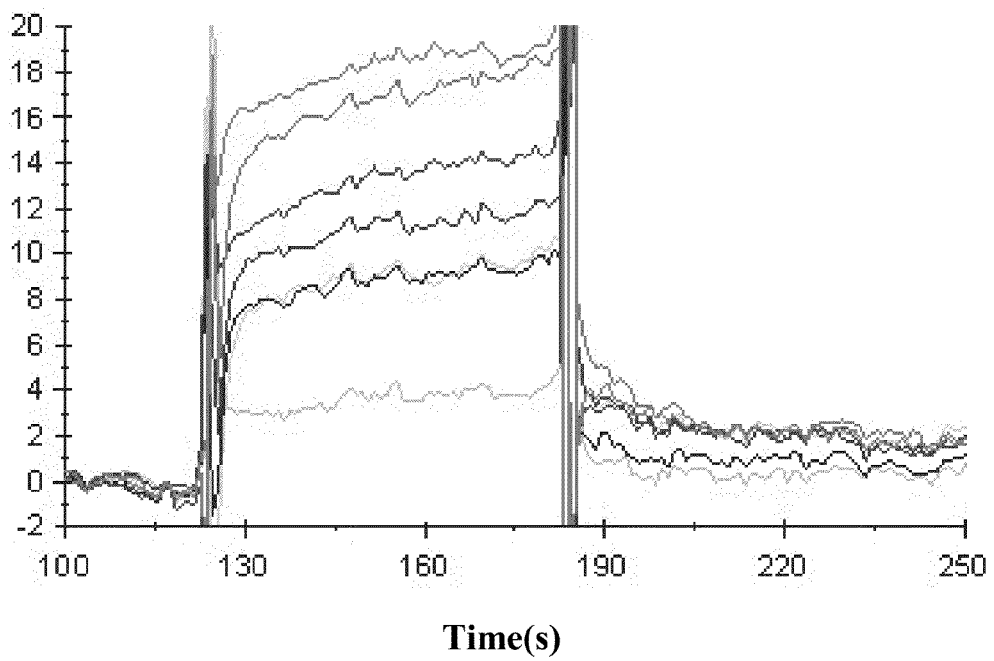
FIG. 2 is a response curve of an interaction between Tiliroside and FP-2 protein by SPR.

The response curves in FIG. 1 and FIG. 2 refer to different concentrations of compounds, which are $1\times10^{-5}$ M, $5\times10^{-6}$ M, $2.5\times10^{-6}$ M, $1.25\times10^{-6}$ M, $6.25\times10^{-7}$ M, $3.125\times10^{-7}$ M, and 0, respectively, from top to bottom.

DETAILED DESCRIPTION OF THE EMBODIMENTS

Examples of preparations and results of pharmacological test of the invention are shown below. The examples do not limit the scope of the invention, but are intended to make the invention more clearly understandable.

Example 1

Preparation of Stenopalustrosides A and D

The plant material (22 kg) of *Abies nephrolepis* was pulverized and extracted with 80% EtOH under reflux for 3×3 h. The extracts were combined and concentrated to a small volume and then partitioned with petro ether (PE), chloroform ($CHCl_3$), ethyl acetate (EtOAc), n-butanol (n-BuOH) and water ($H_2O$), affording the fractions. The EtOAc fraction (480 g) was further separated into six sub-fractions (SF1-SF6) by CC over silica gel (200 mesh) eluting with gradient $CHCl_3/Me_2CO$. SF2 (36.3 g) was subjected to column chromatography (CC) over MCI, Sephadex LH-20, RP-MPLC (eluting with $MeOH/H_2O$) and preparative TLC to give two single compounds, 76 mg and 58 mg, respectively. These two compounds were identified as Stenopalustroside A and Stenopalustroside D, respectively, using LTV, IR, mass, and NMR spectra.

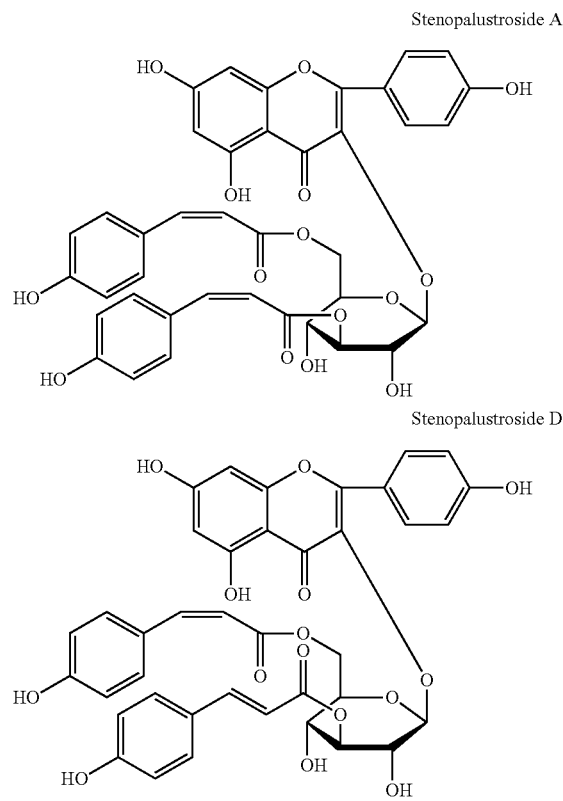

Example 2

Preparation of Tiliroside

SF3 (520 mg) in EXAMPLE 1 was subjected to RP-HPLC (eluting with $MeOH/H_2O$) and preparative TLC to give a single compound, 55 mg. This compound was identified as Tiliroside represented by formula (I) using LTV, IR, mass, and NMR spectra.

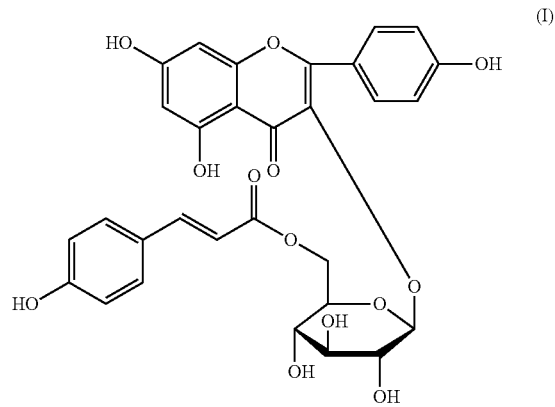

Example 3

Preparation of kaempferol 3-O-β-(6″-caffeoylglucoside)

SF4 (340 mg) in EXAMPLE 1 was subjected to RP-HPLC (eluting with MeOH/H$_2$O) and preparative TLC to give a single compound, 30 mg. This compound was identified as kaempferol 3-O-β-(6″-caffeoylglucoside) represented by formula (II) using UV, IR, mass, and NMR spectra.

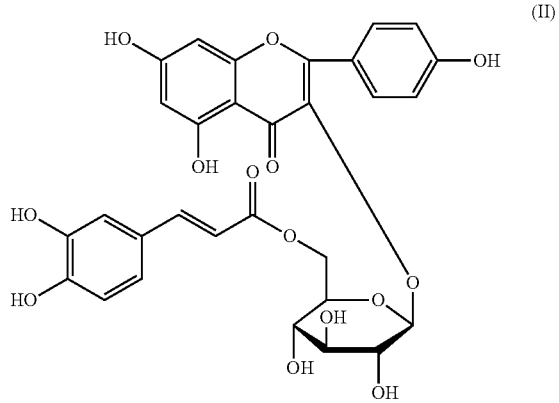

(II)

Example 4

Preparation of kaempferol 3-(2,4-di-E-p-coumaroyl-rhamnoside)

SF6 (1.2 g) in EXAMPLE 1 was subjected to RP-HPLC (eluting with MeOH/H$_2$O) and preparative TLC to give a single compound, 130 mg. This compound was identified as kaempferol 3-(2,4-di-E-p-coumaroyl-rhamnoside) represented by formula (III) using LTV, IR, mass, and NMR spectra.

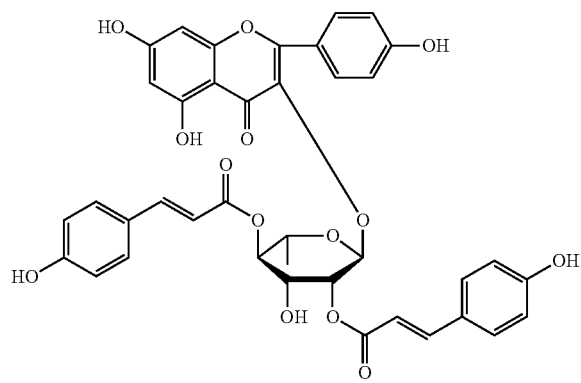

(III)

Example 5

Assay of Binding Activity Between Tiliroside and Falcipain-2 Protease

The screening and kinetics determination of the falcipain-2 protease and tiliroside binding activity are based on SPR mechanism, which employs Biacore 3000 (Biacore AB, Uppsala, Sweden).

(1) The Construction of Falcipain-2 Plasmid (pQE30-Fal2)

Primers were designed according to the falcipain-2 cDNA sequence, utilizing the following primers, forward 5'CGTG-GATCCCAAATGAATTATGAAG3'(SEQ ID NO. 1) and reverse 5'ATATGTCGACTTATTCAATTAATGGAATG3' (SEQ ID NO. 2), which including two restriction sites, BamH I and Sal I The falcipain-2 fragment was amplified by the polymerase chain reaction (PCR), and the PCR product was ligated into the pQE-30 expression vector and then further verified by sequencing. This construct was transformed into *E. coil* M15 (Qiagen).

(2) Expression and Purification of Falcipain-2 Protein

The engineering bacteria were obtained by transforming constructed plasmid pQE30-Fal2 into the *E. coli* M15 cells. They were culturing in LB medium (10 g/L tryptone, 5 g/L yeast extract, 10 g/L sedium chloride) containing ampicillin (100 ng/mL) and kanamtcin (25 ng/mL) for overnight. Then, transfer the bacteria into fresh LB medium (1 L) containing ampicillin and kanamycin (according to 1:100) at 37° C., 220 rpm. When the OD600 reached approximately 0.8, IPTG was added to a final concentration 0.5 mM, and induced at 25° C. for 12 hours. The bacteria were collected by centrifuging at 4,000 rpm for 30 min, and stored the product in −80° C. ultra-low temperature freezer for overnight. The bacteria were suspended by 20 mM buffer (20 mM Tris-HCl, 0.5 M NaCl, and 10 mM imidazole, pH 8.0), and sonicated (power, 300 W, 120 cycles of 5 s each, with cooling for 10 s between the cycles). The broken cells were centrifuged at 10,000 rpm for 30 mM, 4° C., and discarded the supernatant. The pellet was solubilized in 20 mL buffer (6 M guanidine HCl, 20 mMTris-HCl, 250 mM NaCl, 20 mM imidazole, pH 8.0) with gentle stirring at RT for 60 mM, and centrifuged at 10,000 rpm for 30 mM. Transfer the supernatant to the Ni$^{2+}$-NTA column which was equilibrated with the Binding buffer (6M guanidine HCl, 20 mM Tris-Cl, 250 mM NaCl, pH 8.0). The resin was washed with Buffer 1 (8 M urea, 20 mMTris-Cl, 500 mMNaCl, pH 8.0) and Buffer 2 (8 M urea, 20 mM Tris-Cl, 30 mM imidazole, pH 8.0), 30 mL respectively. Bound protein was eluted with 8M urea, 20 mM Tris-Cl, 1M imidazole, pH 8.0, and the eluted protein was analyzed by SDS-PAGE.

(3) The FP-2 Inclusion Bodies Protein Refolding

The purified protein was added 10 mM DTT at 37° C. for 45 mM, and was diluted to 10 g/mL for dialysis overnight (dialysis buffer: 100 mM Tris-Cl, 1 mM EDTA, 20% glycerol, 250 mM L-arginine, 1 mM GSH, 1 mM GSSG, pH 8.0). Protein was concentrated and used for enzyme inhibitory activity determination.

(4) The FP-2 Protein Coupling

The Biacore 3000 instrument was thoroughly cleaned, and was equilibrated with PBS buffer (10 mM 4-hydroxy piperazineethanesulfonic acid, 150 mM NaCl, 3 mM EDTA and 0.005% (v/v) surfactant P20, pH 7.4) to the baseline stability. 0.2M N-ethly-N'-dimethyl aminopropylcarbodiimide and 50 mMM N-hydroxysuccinimide (EDC/NHS) was mixed by 1:1, and injected 7 min at 5 μL/min to activate the chip surface. The FP-2 protein was diluted with 10 mM sodium acetate (pH 4.2) to a final concentration of 69 μg/mL, and the flow rate of injection is 5 μL/min. Finally, utilizing 1M hydrochloric acid ethanol amine (pH 8.5) to inject for 7 min at 5 μL/min to block the chip surface, and the FP-2 protein signal was about 9300 RU.

(5) Compound Screening

The substrate Z-Phe-Arg-pNAHCl (Bachem AG) served as a positive control. Tiliroside (prepared from EXAMPLE 2) was solubilized in 100% DMSO and the concentration of tiliroside was 10 mM. The compounds were diluted with HBS-EP buffer to the final concentration of 1 μM and 10 μM, respectively, and the final concentration of DMSO was 0.1%. According to the RU (Response Unit) value of tilirosideand FP-2 protein binding, it can determine whether a compound has a binding activity. The compounds with binding activity would conduct the further detailed kinetic experiments. The results suggested that tiliroside and FP-2 protein have obvious binding activity.

(6) Dynamics Assay

Tiliroside, using assay buffer HBS-EP, was prepared for different concentration gradient, and injected at 30 μL/min for 1 min and dissociated for 2 mM. Use the same buffer to stabilize it for 2 mM and we obtained the sensing chart of the tiliroside and FP-2 protein interaction. Then fitting with the Biacore analysis software 1:1 combination model or stable models to obtain precise kinetic and thermodynamic constants.

(7) Results

TABLE 1

Test results of the positive control and tiliroside and FP-2 protein binding constant

| Number | Compound | $K_D$ (μM) |
|---|---|---|
| 1 | Tiliroside | 5.57 |
| 2 | Z-Phe-Arg-pNAHCl | −32.1 |

Example 6

Percentage Inhibition Determination of Representative Compounds Against Falcipain-2 Protease (1) Expression and Purification of Falcipain-2 and Refolding of FP-2 Inclusion Bodies Protein See EXAMPLE 5

(2) The Determination of the Invention Compounds' Inhibitory Activity Against FP-2

FP-2 protein and test compounds dissolved in DMSO (prepared from EXAMPLES 1-4) were added to 197 μL, buffer, containing 100 mM NaOAc, 10 mM DTT, pH 5.5 (final concentration 10 μg/mL). The test compound were Stenopalustroside A, Stenopalustroside D, Tiliroside, kaempferol 3-O-β-(6″-caffeoylglucoside) and kaempferol 3-(2,4-di-E-p-coumaroyl-rhamnoside), respectively, which final concentration were 10 μM and 0 μM (as negative control). These compounds were incubated for 30 mM and employed MD SpectraMax M5 Microplate Reader to continuous detect the RFU for 15 min, at excitation 355 nm and emission 460 nm Calculate the reaction rate $K_m$, and obtain percentage inhibitory rate of the test compound at 10 μM by the following equation, The equation is:

($K$mof control group−$K$mof experimental group)/ $K$mof control group×100%

TABLE 2

Assay Results of Compounds Activity

| Number | Compounds | Inhibition rate (%, 10 μM) |
|---|---|---|
| 1 | Stenopalustroside A | 53.03 |
| 2 | Stenopalustroside D | 39.4 |

TABLE 2-continued

Assay Results of Compounds Activity

| Number | Compounds | Inhibition rate (%, 10 μM) |
|---|---|---|
| 3 | Tiliroside | 64.36 |
| 4 | kaempferol 3-O-β-(6″-caffeoylglucoside) | 53.03 |
| 5 | kaempferol 3-(2,4-di-E-p-coumaroyl-rhamnoside) | 49.37 |

Example 7

Half Maximal Inhibitory Concentration (IC50) Assay of the Invention Compounds Against FP-2 Protease Select 10 M compounds with over 50% inhibitory rate to detect $IC_{50}$, and utilize the compound solutions prepared from EXAMPLE 1 to EXAMPLE 4, Stenopalustroside A, tiliroside kaempferol 3-O-β-(6″-caffeoylglucoside), and the experimental methods and system followed as EXAMPLE 6. According to FP-2 activity reaction rate $K_m$ with compounds at different concentrations, we can calculate the inhibitory rate of compounds against FP-2 at different concentration. The $IC_{50}$ value was fitted with utilizing the Sigmoidal Equation by Origin software. Results are shown in Table 3.

TABLE 3

Inhibitory activities IC50 value of falvonoids against falcipain-2

| NO. | Name | $IC_{50}$ (μM) |
|---|---|---|
| 1 | Stenopalustroside A | 1.45 |
| 2 | Tiliroside | 13.13 |
| 3 | kaempferol 3-O-β-(6″-caffeoylglucoside) | 13.52 |

The results showed that above flavonoids have inhibitory activities against FP-2, and indicated that these compounds have anti-malarial activity.

Example 8

In Vitro Anti-Malarial Activity Assay

In vitro anti-malarial activity of the representative compounds was determined against chloroquine sensitive (D6) and chloroquine-resistant (W2) strains of *P. falciparum*.

The anti-malarial activity was determined by measuring plasmodial LDH activity as described earlier (Jain, M.; Khan, S. I.; Tekwani, B. L.; Jacob, M. R.; Singh, S.; Singh, P. P.; Jain, R. Synthesis, anti-malarial, antileishmanial, and antimicrobial activities of some 8-quinolinamine analogues. *Bioorg. Med. Chem.* 2005, 13, 4458-4466). A suspension of red blood cells infected with D6 or W2 strains of *P. falciparum* (200 with 2% parasitemia and 2% hematocrit in RPMI 1640 medium supplemented with 10% human serum and 60 lg/mL Amikacin) was added to the wells of a 96-well plate containing 10 μL of serially diluted test samples. The plate was flushed with a gas mixture of 90% $N_2$, 5% $O_2$, and 5% $CO_2$ and incubated at 37° C. for 72 h in a modular incubation chamber (Billups-Rothenberg, Calif.). Parasitic LDH activity was determined by using Malstat™ reagent (Flow Inc., Portland, Oreg.) according to the procedure of Makler and Hinrichs (M. T. Makler and D. J. Hinrichs, Measurement of the lactate dehydrogenase activity of *Plasmodium falciparum* as an assessment of parasitemia. *J. Am. J. Trop. Med. Hyg.* 1993, 48(2):205-210). Briefly, 20 μl, of the incubation mixture was mixed with 100 μL of the Malstat™ reagent and incubated at room temperature for 30 min Twenty microliters of a 1:1 mixture of NBT/PES (Sigma, St. Louis, Mo.) was then added and the plate was further incubated in the dark for 1 h. The reaction was then stopped by the addition of 100 μL of a 5% acetic acid solution. The plate was read at 650 nm. Artemisinin and chloroquine were included in each assay as the drug controls. $IC_{50}$ values were computed from the dose-response curves. To determine the selectivity index of anti-malarial activity of compounds, their cytotoxicity in vitro to mammalian cells was also determined. The assay was performed in 96-well tissue culture-treated plates as described earlier (J. Mustafa, S. I. Khan, G. Ma, L. A. Walker and I. A. Khan, Synthesis and Anticancer Activities of Fatty Acid Analogs of Podophyllotoxin. *Lipids*. 2004, 39(2):167-172). Vero cells (monkey kidney fibroblasts) were seeded to the wells of 96-well plate at a density of 25,000 cells/well and incubated for 24 h. Samples at different concentrations were added and plates were again incubated for 48 h. The number of viable cells was determined by Neutral Red assay. $IC_{50}$ values were obtained from dose-response curves. Doxorubicin was used as a positive control. The result showed that the representative flavonoid glycoside compounds exhibited potential anti-malarial activity against *P. falciparum*, D6 and W2 strain.

TABLE 4

In vitro Anti-malarial activity of the representative flavonoid glycoside compounds

| Compound | *P. falciparum* (D6 Clone) IC50 (μM) | *P. falciparum* (W2 Clone) IC50 (μM) |
|---|---|---|
| Stenopalustroside A | 32.8 | 98.6 |
| Stenopalustroside D | 68.4 | 165 |
| Tiliroside | 123 | 106 |
| kaempferol 3-O-β-(6″-caffeoylglucoside) | 55.8 | 91.3 |
| kaempferol 3-(2,4-di-E-p-coumaroyl-rhamnoside) | 45.1 | 147 |
| Chloroquine | <26.4 | 160 |
| Artemisinine | <26.4 | <26.4 |

Example 9

In Vivo Anti-Malarial Activity Assay

Tests were performed in a 4-day suppressive standard test using the methods of David, Thurston and Peters (David, A. F., Philip, J. R., Simon, L. C., Reto B., and Solomon N. Antimalarial drug discovery: Efficacy models for compound screening. *Nature Reviews*. 2004; 3: 509-520). The *plasmodium* species, that is most widely employed in rodent malaria parasite-*Plasmodium berghei* (chloroquine sensitive strain), was used to infect Swiss albino mice for a fourday suppressive test. The *P. berghei* was subsequently maintained in the laboratory by serial blood passage from mouse to mouse. For the study, a donor mouse with a rising parasitemia of 20% was sacrificed and its blood was collected in a slightly heparinized syringe from the auxiliary vessels. The blood was diluted with Trisodium Citrate (TC) medium so that each 0.2 ml contained approximately 107 infected red cells. Each animal received inoculums of about 10 million parasites per gram body weight, which is expected to produce a steadily rising infection in mice.

Male Swiss albino mice were used. The mice were allowed to acclimatize to the laboratory environment under a controlled temperature of 20° C. and at optimum humidity for at least three days before being subjected to the experiments. All of the mice were divided into groups of six, and infected with malaria parasites.

The infection of the recipient mice was initiated by needle passage of the above mentioned parasite preparation, from the donor to healthy test animals via an intraperitoneal route. Therefore, *P. berghei* infected red blood cells were intraperitoneally injected into the mice from the blood diluted with TC medium so that each 0.2 ml had approximately 106-107 infected red cells (parasite per kg of body weight). Each mouse was infected with single inoculums of 0.2 ml blood.

The 4-day procedures were started on Mondays while blood smears for parasitemia were collected on Fridays. The infected mice were weighed, randomly divided into treatment, vehicle and standard drug groups. The treatment group received the representative flavonoid glycoside compounds (10-200 mg/kg) daily for 4 days, starting on the same day as that of the parasite inoculation. The compounds were administered through intra gastric route using the stomach tube to ensure the safe ingestion of the compounds and the vehicle.

Thin smears of blood films were obtained from the peripheral blood on the tail from each mouse on day four after infection. The smears were placed on microscopic slides, fixed with methanol and stained with Gemsa at pH 7.2, for parasitemia. The microscope had an Ehrlich's eyepiece and a nose diaphragm showing about 100 red blood cells per field. The number of parasitized erythrocytes in each of the 10-50 such fields were counted three times and the average was calculated to give the Parasitemia of each individual animal. Percentage of suppression was calculated by using the following formula.

% Suppression=(Parasitemia in negative control−Parasitemia in study group)/Parasitemia in negative control The result showed that Stenopalustroside D (EXAMPLE 1) and Tiliroside (EXAMPLE 2) exhibited potential in vivo anti-malarial activity against *P. berghei*, with the maximum suppression ratio of 60%.

TABLE 5

In vivo Anti-malarial activity of the representative flavonoid glycoside compounds

| Groups | Dose (mg/kg) | Day 4 % Suppression | Day 5 % Suppression | Day 6 % Suppression |
|---|---|---|---|---|
| Control | — | — | — | — |
| Chloroquine | 10 | 100 | 100 | 100 |
| Stenopalustroside A | 10 | — | — | — |
|  | 50 | — | — | — |
|  | 100 | — | — | — |
|  | 200 | 34.7 | 33.3 | 18.9 |
|  | 400 | — | — | — |
| Stenopalustroside D | 10 | 30.4 | 51.5 | 32.4 |
|  | 50 | 60.8 | 63.6 | 58.3 |
|  | 100 | 56.5 | 60.6 | 45.9 |
|  | 200 | 43.4 | 42.4 | 37.8 |
|  | 400 | 8.6 | 24.2 | 13.5 |
| Tiliroside | 10 | 39.1 | 51.5 | 35.1 |
|  | 50 | 56.5 | 64.0 | 54.0 |
|  | 100 | 34.7 | 39.3 | 21.6 |
|  | 200 | 21.7 | 30.3 | 18.9 |
|  | 400 | — | 9.0 | — |
| kaempferol 3-O-β-(6″-caffeoylglucoside) | 10 | 20.6 | 27.2 | 37.8 |
|  | 50 | 52.1 | 54.5 | 45.9 |
|  | 100 | 13.0 | 15.1 | 10.8 |
|  | 200 | 4.3 | 9.0 | 5.4 |
|  | 400 | — | 6.0 | — |
| kaempferol 3-(2,4-di-E-p-coumaroyl-rhamnoside) | 10 | — | — | — |
|  | 50 | 34.7 | 24.2 | 29.7 |
|  | 100 | 13.0 | 21.2 | 24.3 |
|  | 200 | — | 9.0 | 5.4 |
|  | 400 | — | — | — |

The invention claimed is:

1. A method for treatment of malaria comprising administering to a patient in need thereof a pharmaceutically effective amount of a flavonoid glycoside compound represented by formula (A) or (B),

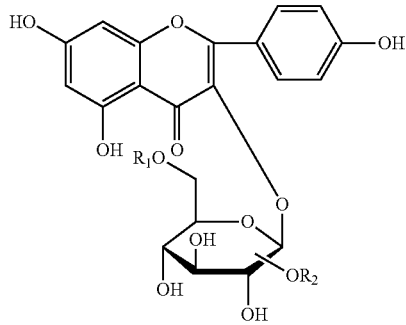

(A)

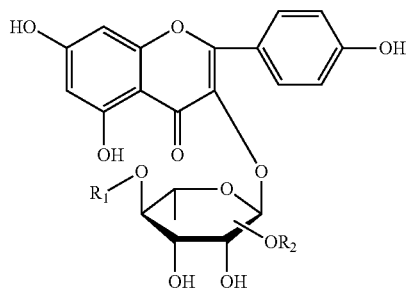

(B)

wherein $R_1$ is coumaroyl, transcoumaroyl, or caffeoryl; and $R_2$ is coumaroyl, transcoumaroyl, caffeoryl, or H.

2. The method of claim 1, wherein the flavonoid glycoside compound is prepared by extraction from herb or by chemical synthesis.

3. The method of claim 1, wherein the malaria is caused by *plasmodium*.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Fully-synthetic forward primer for falcipain-2 fragment amplification

<400> SEQUENCE: 1
cgtggatccc aaatgaatta tgaag                                  25

<210> SEQ ID NO 2
<211> LENGTH: 29
<212> TYPE: DNA
<213> ORGANISM: Artificial Sequence
<220> FEATURE:
<223> OTHER INFORMATION: Fully-synthetic reverse primer for falcipain-2 fragment amplification

<400> SEQUENCE: 2
atatgtcgac ttattcaatt aatggaatg                              29